US009354207B2

(12) United States Patent
Buendia Garcia et al.

(10) Patent No.: US 9,354,207 B2
(45) Date of Patent: May 31, 2016

(54) BOIL AND BOIL-DRY DETECTION METHODS FOR COOKING APPLIANCES USING VIBRATION SENSORS

(71) Applicant: Whirlpool Corporation, Benton Harbor, MI (US)

(72) Inventors: Ali R. Buendia Garcia, St. Joseph, MI (US); Farhad Ashrafzadeh, Bowling Green, KY (US); Moeed Mukhtar, St. Joseph, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 635 days.

(21) Appl. No.: 13/649,155

(22) Filed: Oct. 11, 2012

(65) Prior Publication Data

US 2014/0057214 A1    Feb. 27, 2014

Related U.S. Application Data

(63) Continuation-in-part of application No. 13/591,692, filed on Aug. 22, 2012.

(51) Int. Cl.
| | |
|---|---|
| *F23N 1/02* | (2006.01) |
| *A47J 27/62* | (2006.01) |
| *F24H 9/20* | (2006.01) |
| *G01N 29/46* | (2006.01) |
| *F23N 5/24* | (2006.01) |
| *F23D 14/06* | (2006.01) |
| *F23D 14/72* | (2006.01) |
| *G01N 29/14* | (2006.01) |
| *G01N 29/44* | (2006.01) |

(52) U.S. Cl.
CPC .............. *G01N 29/46* (2013.01); *F23D 14/06* (2013.01); *F23D 14/72* (2013.01); *F23N 5/242* (2013.01); *G01N 29/14* (2013.01); *G01N 29/4427* (2013.01); *G01N 29/4454* (2013.01); *F23N 2031/00* (2013.01)

(58) Field of Classification Search
USPC ......... 126/374.1, 351.1; 431/12; 99/326, 330, 99/331; 374/E11.009
See application file for complete search history.

(56) References Cited

U.S. PATENT DOCUMENTS

| | | | | |
|---|---|---|---|---|
| 4,869,233 | A * | 9/1989 | Stulen ..................... | A47J 27/62 126/374.1 |
| 5,096,725 | A * | 3/1992 | Kim .............................. | 426/233 |
| 6,118,104 | A * | 9/2000 | Berkcan ............... | H05B 1/0269 219/481 |
| 6,433,693 | B1 * | 8/2002 | Mathews, Jr. ................. | 340/584 |
| 2012/0186745 | A1 * | 7/2012 | Miya ................. | H01J 37/32715 156/345.27 |

* cited by examiner

*Primary Examiner* — Avinash Savani
*Assistant Examiner* — Vivek Shirsat

(57) ABSTRACT

A method of boil and boil-dry detection for appliances. The method includes the steps: detecting vibrations that correspond to cookware situated on a burner assembly; generating a vibration signal based on the vibrations; and performing signal processing on the vibration signal. The method also includes the steps: collecting vibration data related to the vibration signal; and detecting boiling and boil-dry conditions for a liquid contained within the cookware based at least in part on an evaluation of the vibration data. The method may also include the steps: indicating the boiling and boil-dry conditions; and controlling the burner assembly based at least in part on the boiling and boil-dry conditions.

6 Claims, 6 Drawing Sheets

BOIL AND BOIL-DRY DETECTION METHODS FOR COOKING APPLIANCES USING VIBRATION SENSORS

CROSS-REFERENCE TO RELATED APPLICATION

This application is a continuation-in-part of U.S. patent application Ser. No. 13/591,692, filed on Aug. 22, 2012, entitled "BOIL AND BOIL-DRY DETECTION SYSTEMS FOR COOKING APPLIANCES USING VIBRATION SENSORS." The aforementioned related application is hereby incorporated by reference.

TECHNICAL FIELD

The disclosure relates to cooking appliances and, more particularly, to cooking sensor systems and methods employing vibration sensors for use in such appliances.

BACKGROUND

Cooking operations involving foods, mixtures, edibles, soups, liquids and other preparations with substantial liquid content often require a boiling step. Depending on the food composition (i.e., solid and liquid components), recipe and various other cooking-related factors, a short or prolonged boiling step may be required. The boiling temperature of the liquid component of a food substance is dependent on atmospheric conditions, the composition of the liquid itself, condition of the cookware, and other factors. Typically, the cooking operations necessary to boil such substances involve manual control and oversight of a heating input, e.g., a gas burner control knob, an electric heating element input, etc. In particular, an operator, through visual and/or auditory indications, detects a boiling condition and controls the heating input, accordingly.

BRIEF SUMMARY

One aspect of the disclosure is to provide a method of boil and boil-dry detection for cooking appliances. The method includes the steps: detecting vibrations that correspond to cookware situated on a burner assembly; generating a vibration signal based on the vibrations; and performing signal processing on the vibration signal. The method also includes the steps: collecting vibration data related to the vibration signal; and detecting boiling and boil-dry conditions for a liquid contained within the cookware based at least in part on an evaluation of the vibration data.

Another aspect of the disclosure is to provide a method of boil and boil-dry detection for cooking appliances. The method includes the steps: detecting vibrations that correspond to cookware situated on a burner assembly; generating a vibration signal based on the vibrations; and performing signal processing on the vibration signal. The method also includes the steps: collecting vibration data related to the vibration signal; detecting boiling and boil-dry conditions for a liquid contained within the cookware based at least in part on an evaluation of the vibration data; and indicating the boiling and boil-dry conditions.

A further aspect of the disclosure is to provide a method of boil and boil-dry detection for cooking appliances. The method includes the steps: detecting vibrations that correspond to cookware situated on a burner assembly; generating a vibration signal based on the vibrations; and performing signal processing on the vibration signal. The method also includes the steps: collecting vibration data related to the vibration signal; detecting boiling and boil-dry conditions for a liquid contained within the cookware based at least in part on an evaluation of the vibration data; and controlling the burner assembly based at least in part on the boiling and boil-dry conditions.

These and other features, advantages, and objects of the disclosure will be further understood and appreciated by those skilled in the art by reference to the following specification, claims, and appended drawings.

DETAILED DESCRIPTION

For purposes of description herein, the aspects of this disclosure may assume various alternative orientations, except where expressly specified to the contrary. The specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

In general, boiling operations, when not well-monitored and/or controlled by an operator, can result in spattering and/or over-cooking of substances with substantial liquid content. Further, over-boiling (i.e., boiling in excess of the intended duration) may lead to vaporization of all liquid components within the substance subjected to the boiling operation within the cookware (i.e., a "boil-dry" condition). A boil-dry condition often will damage the cookware, particularly cookware comprising materials not designed for temperatures in excess of the boiling point for water and other food-related liquids under ambient atmospheric conditions. Even if the base material of the cookware is fabricated from metals, ceramics or other materials that are less susceptible to temperature-related damage, many food-safe coatings applied to cookware to reduce food adhesion are more susceptible to damage from the cookware temperatures associated with a boil-dry condition.

Over-boiling of food-related substances with high liquid content also leads to excess energy usage because the boiling operation is conducted longer than necessary for the given substance. Even well-controlled boiling operations are often not performed in an energy efficient manner. This is because, in many cases, the energy required to sustain a boiling condition is lower than the energy needed to reach the boiling temperature for a given food substance.

Figure 1:
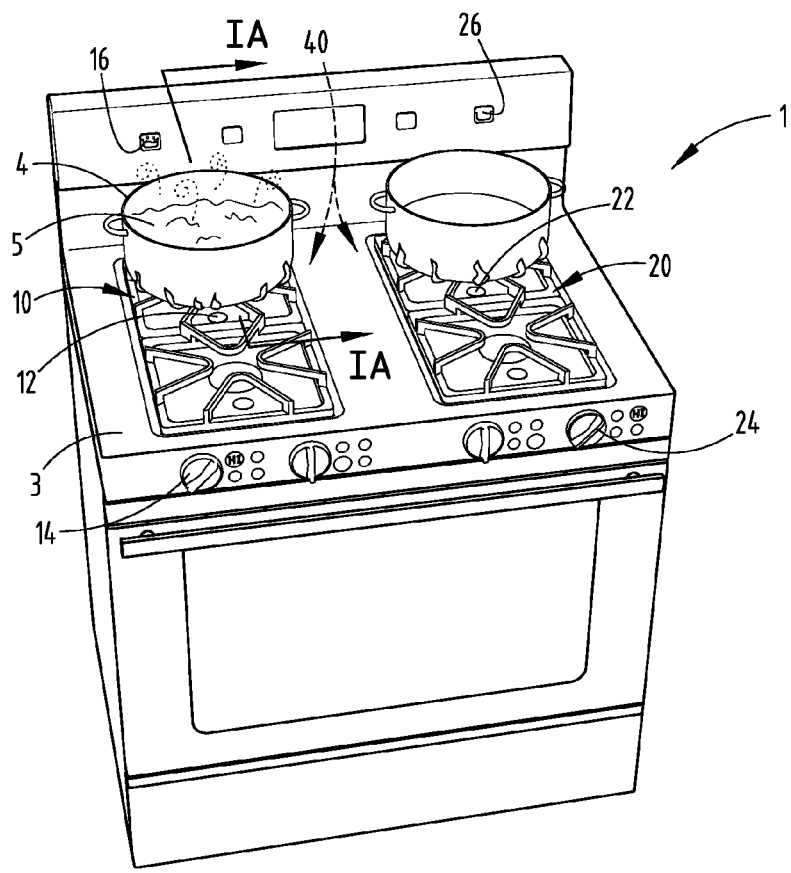
FIG. 1 is a perspective view of a cooking range with four gas burners configured with a cooking sensor detection system according to one embodiment.

A cooking sensor system configured to assist an operator in conducting boiling operations has been developed to remedy the foregoing problems. These cooking sensor systems can be employed in various cooking appliances, including but not limited to electric-, gas- and induction-based appliances configured for the preparation of food with high liquid content. Referring to FIG. 1, a cooking range 1 is depicted with an exemplary cooking sensor system, i.e., sensor system 40. Cooking range 1 includes cook-top surface 3 and four standard gas burners. Cooking range 1 and, more particularly, sensor system 40, includes left rear burner assembly 10 and right rear burner assembly 20. Burner assemblies 10 and 20 can be controlled by left rear burner knob 14 and right rear burner knob 24, respectively. In particular, an operator may adjust knobs 14 and 24 to direct various amounts of gas to the burner assemblies 10 and 20 to effect flame and heating control during cooking operations. Both burner assemblies 10 and 20 are depicted in FIG. 1 with a "HI" heat input.

A pot 4 rests on each of the burner assemblies 10 and 20. The pot 4 resting on left rear burner assembly 10 depicts a food-related liquid 5 in a boiling condition. The pot 4 resting on right rear burner assembly 20 is empty, despite the presence of a "HI" heat input from right rear burner knob 24. Accordingly, the pot 4 over burner assembly 20 is likely subject to a boil-dry condition (i.e., food-related liquid 5 has been vaporized).

As also shown in FIG. 1, cooking sensor system 40 further includes left rear burner sensor assembly 12 and right rear burner sensor assembly 22. Further, sensor assemblies 12 and 22 are located in proximity to burner assemblies 10 and 20, respectively, and are configured to generate vibration signals that correspond to vibrations associated with the pot 4 situated on the burner assemblies 10 and 20. Sensor assemblies 12 and 22, however, may be located at various locations within cooking range 1, on cook-top surface 3 or on burner assemblies 10 and 20 to generate these vibration signals.

Further, sensor assemblies 12 and 22 can include, but are not limited to, 1D, 2D and 3D accelerometers, tilt sensors, proximity sensors, displacement sensors and other types of transducers and piezoelectric elements. Various combinations are possible that optimize vibration sensitivity, heat-resistance, cost and other considerations related to the cooking sensor system 40. Still further, cookware, such as pot 4, may also be embedded with wireless vibration sensors for use in sensor assemblies 12 and 22.

FIG. 1 also depicts left rear and right rear burner indicator elements 16 and 26 situated on an upper surface of cook-top surface 3. Indicator elements 16 and 26 are associated with burner assemblies 10 and 20, respectively. Further, indicator elements 16 and 26 may be configured to visually indicate boiling and boil-dry conditions for pots (e.g., pot 4 or other suitable cookware containing food-related liquids) located on burner assemblies 10 and 20, among other indications associated with sensor system 40. The indicator elements 16 and 26 may also be configured to provide auditory signals associated with such boiling and boil-dry conditions. As shown in FIG. 1, the symbol depicted on indicator element 16 corresponds to the boiling condition of the food-related liquid 5 contained in the pot 4 situated on left rear burner assembly 10. Similarly, the symbol depicted on indicator element 26 corresponds to the boil-dry condition of the pot 4 situated on right rear burner assembly 20.

Figure 1A:
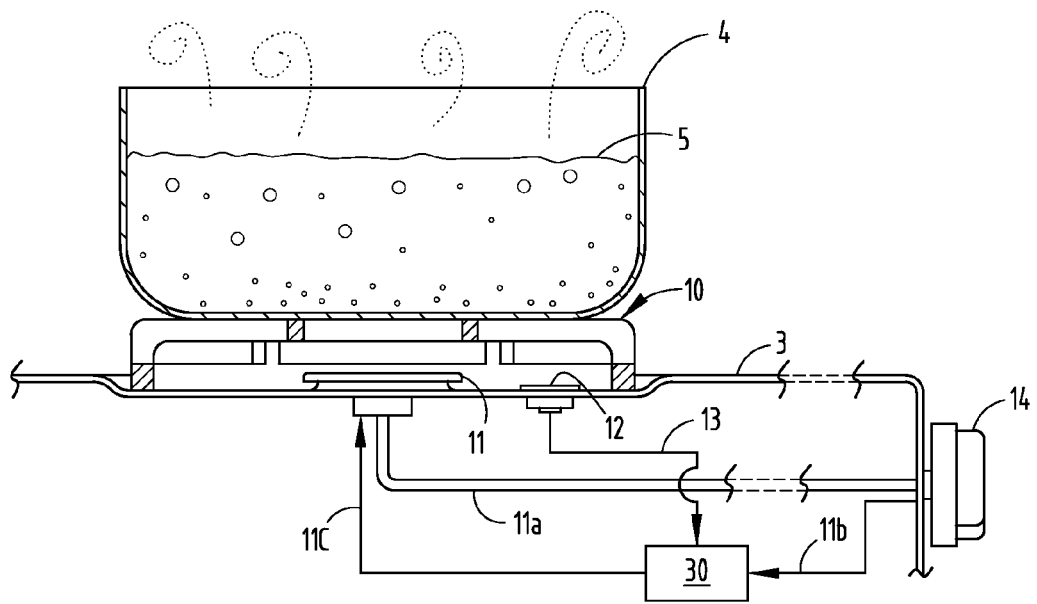
FIG. 1A is side, cross-sectional view of the left rear burner assembly of the cooking range depicted in FIG. 1.

Further aspects of cooking sensor system 40 are depicted in FIG. 1A, a side, cross-sectional view of the left rear burner assembly 12 of the cooking range 1 depicted in FIG. 1. As shown, vibration sensor assembly 12 can be located in proximity to burner assembly 10, and is mounted to cook-top surface 3. Sensor assembly 12 can be coupled to processor 30 via left rear sensor assembly wiring 13. Consequently, vibration signals generated by sensor assembly 12 associated with the pot 4 situated on burner assembly 10 are received by processor 30.

For its part, processor 30 can be arranged to determine boiling and/or boil-dry conditions for the food-related liquid 5 contained within pot 4 (situated on burner assembly 10) based at least in part on the vibration signals received from sensor assembly 12. These conditions can then be indicated to an operator by illumination and/or activation of indicator elements coupled to processor 30, including indicator element 16 (as shown in FIG. 1). Similarly, sensor assembly 22 (not shown in FIG. 1A) may be coupled to processor 30; and, accordingly, processor 30 can determine boiling and boil-dry conditions for liquids in pot 4 situated on burner assembly 20 based at least in part on vibration signals received from sensor assembly 22.

Left rear burner knob 14 is also shown in FIG. 1A, as coupled to left rear burner control element 11 via connection 11a. An operator may adjust left rear burner knob 14 to effect gas, electric, and/or other heat input to left rear burner control element 11 through connection 11a. Accordingly, burner control element 11 (and other burner control elements associated with range 1) may consist of gas, electric and induction-based heating elements. Connection 11a, for example, may consist of gas tubing and valving (not shown) arranged to provide a gas supply to burner control element 11 (when configured as a gas burner) through operation of left rear burner knob 14. Connection 11a may also consist of electrical wiring configured to control a resistance- or other electric-based burner control elements 11 for the same purpose.

FIG. 1A also depicts connection 11b, optionally arranged to couple processor 30 to left rear burner knob 14. Essentially, connection 11b provides a signal to processor 30 from knob 14 that is associated with the amount of gas, electric or induction-related input to burner assembly 10 from knob 14. Consequently, processor 30 can determine boiling and/or boil-dry conditions for food-related liquid 5 within pot 5 based at least in part on the vibration signals from sensor assembly 12 and heat input signals from left rear burner knob 14 via connection 11b. Although not shown, processor 30 can also rely on vibration signals from sensor assembly 22 and/or heat input signals from right rear burner knob 24 for the same or a similar purpose.

FIG. 1A further depicts optional connection 11c, arranged to couple processor 30 to left rear burner control element 11. Connection 11c can allow processor 30 to provide some operational control over the burner control element 11. Management of burner control element 11 by processor 30 may be based at least in part on a boiling and/or boil-dry condition determined by the processor 30. For example, processor 30 may override or adjust an operator's heat input from knob 14 to burner control element 11 based on the detection of a boiling condition. Similarly, processor 30 may override an operator's heat input from knob 14 to burner control element 11 based on the determination of a boil-dry condition. Various types of control can be effectuated by processor 30 in this manner to provide better energy utilization, adherence to a user-desired boiling duration, protection of cookware from boil-dry conditions, avoidance of spatter, and other user-assisted cooking benefits.

Figure 2A:
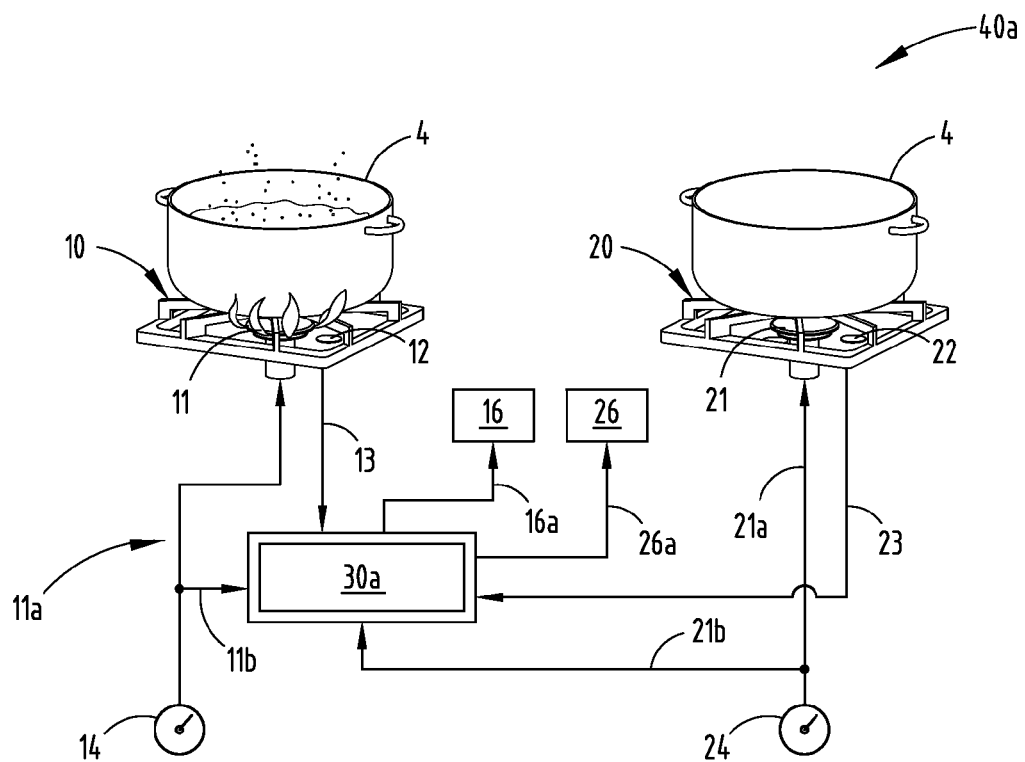
FIG. 2A is a schematic depicting a cooking sensor system that includes burner assemblies, vibration sensor assemblies, a processor, and indicator elements arranged to indicate boiling and boil-dry conditions according to another embodiment.
Figure 2B:
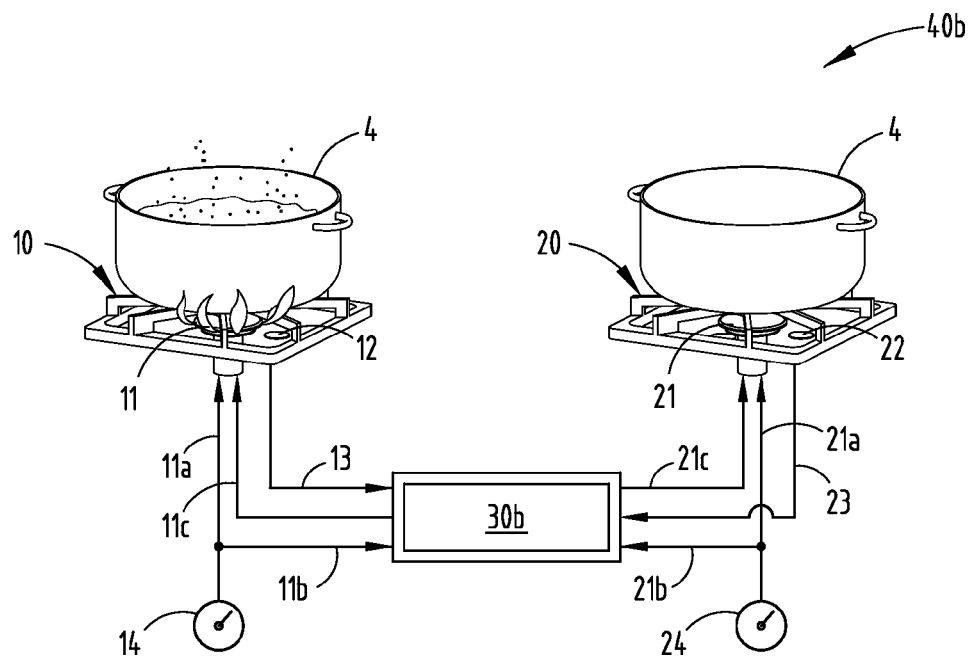
FIG. 2B is a schematic depicting a cooking sensor system that includes burner assemblies, vibration sensor assemblies, a processor, and a control element arranged to control the operation of the burner assemblies based at least in part on the presence of boiling and boil-dry conditions according to a further embodiment.

Cooking sensor systems 40a and 40b are depicted in FIGS. 2A and 2B, respectively. Cooking sensor system 40a (FIG. 2A) includes burner assemblies 10 and 20, vibration sensor assemblies 12 and 22, processor 30a, and indicator elements 16 and 26. Burner assemblies 10 and 20 can include burner control elements 11 and 21, respectively. Further, left rear burner knob 14 and right rear burner knob 24 elements are coupled to burner control elements 11 and 21 via connections 11a and 21a, respectively. Knobs 14 and 24 can be used to control heat input to control elements 11 and 21 via connections 11a and 21a, respectively. In general, these elements operate and perform in a fashion comparable to the same elements described in connection with the cooking sensor system 40 depicted in FIGS. 1 and 1A.

FIG. 2A depicts various input connections and couplings for processor 30a. For example, vibration signals from sensor assemblies 12 and 22 can be received by processor 30a via wiring 13 and 23 elements. Similarly, heat inputs from knobs 14 and 24 can be received by processor 30a through connections 11b and 21b. As shown, processor 30a can determine boiling and/or boil-dry conditions associated with food-related liquid 5 (not shown) within pots 4 placed on burner assemblies 10 and/or 20 based at least in part on the vibration data from sensor assemblies 12 and 22. Optionally, heat input data from knobs 14 and 24 can also be utilized by processor 30a for this purpose.

Upon a determination of a boiling and/or boil-dry condition, cooking sensor system 40a can then provide an indication of the condition to an operator via indicator elements 16 and 26. In particular, processor 30a can provide visual indications (i.e., "BOILING", "BOIL-DRY") to indicator elements 16 and 26 via connections 16a and 26a. Processor 30a may also send comparable audio indications corresponding to boiling and/or boil-dry conditions to indicator elements 16 and 26.

Cooking sensor system 40b, as shown in FIG. 2B, possesses a configuration similar to sensor system 40a (see FIG. 2A). In particular, 40b includes many of the same elements as 40a (e.g., burner assemblies 10 and 20, and sensor assemblies 12 and 22). However, cooking sensor system 40b can also include a processor 30b, coupled via connections 11c and 21c to burner control elements 11 and 21, respectively. Further, configuration 40b, as shown in FIG. 2B, does not include any indicator elements.

Accordingly, processor 30b may determine boiling and/or boil-dry conditions associated with food-related liquid 5 (not shown) within pots 4 placed on burner assemblies 10 and/or 20 based at least in part on the vibration data from sensor assemblies 12 and 22. However, configuration 40b does not provide the boiling and/or boil-dry information to the operator. Rather, processor 30b can provide further control of burner assemblies 10 and 20 via burner control elements 11 and 21 based on the presence of boiling and/or boil-dry conditions. For example, control element 11 can override a heat input from knob 14 to burner assembly 10 based on a direction from processor 30b in response to the detection of a boiling and/or boil-dry condition. This direction can be used by processor 30b to reduce the likelihood of damage to pot 4 from the boil-dry condition, for example. Likewise, processor 30b can direct control element 11 to operate burner assembly 10 to optimize energy usage once a boiling condition has been detected (based on input data from sensor assembly 12).

Cooking sensor system embodiments with various combinations of the components associated with configurations 40a and 40b depicted in FIGS. 2A and 2B are also feasible. For example, configurations 40a and 40b may be fully combined. A processor 30a (or 30b) arranged in a combined cooking sensor system configuration can provide an indication of a boiling and/or boil-dry condition to indicator elements 16 and/or 26. Further, the processor 30a in the combined configuration can also effectuate control of the heat inputs to burner assemblies 10 and/or 20 via control elements 11 and 22, for example, based on the detection of boiling and/or boil-dry conditions.

Still further, configurations 40a and 40b can be configured to operate in connection with one, some or all of the burner assemblies associated with a given cooking appliance. When associated with one burner assembly, for example, a cooking sensor system 40a need only include one sensor assembly. It is also possible for a cooking sensor system, such as 40a, to be associated with a single burner assembly, while relying at the same time on vibration data from more than one sensor assembly arrayed on or within cooking range 1 (not shown). Conversely, the cooking sensor system 40a may also be configured to determine boiling and/or boil-dry conditions for multiple burner assemblies based on input from only one sensor assembly located on or within range 1 (or a quantity of sensor assemblies that number less than the quantity of burner assemblies). For example, sensor assemblies can provide multiple vibration data vectors that relate to vibration data associated with different locations on the cooking range 1.

Figure 3:
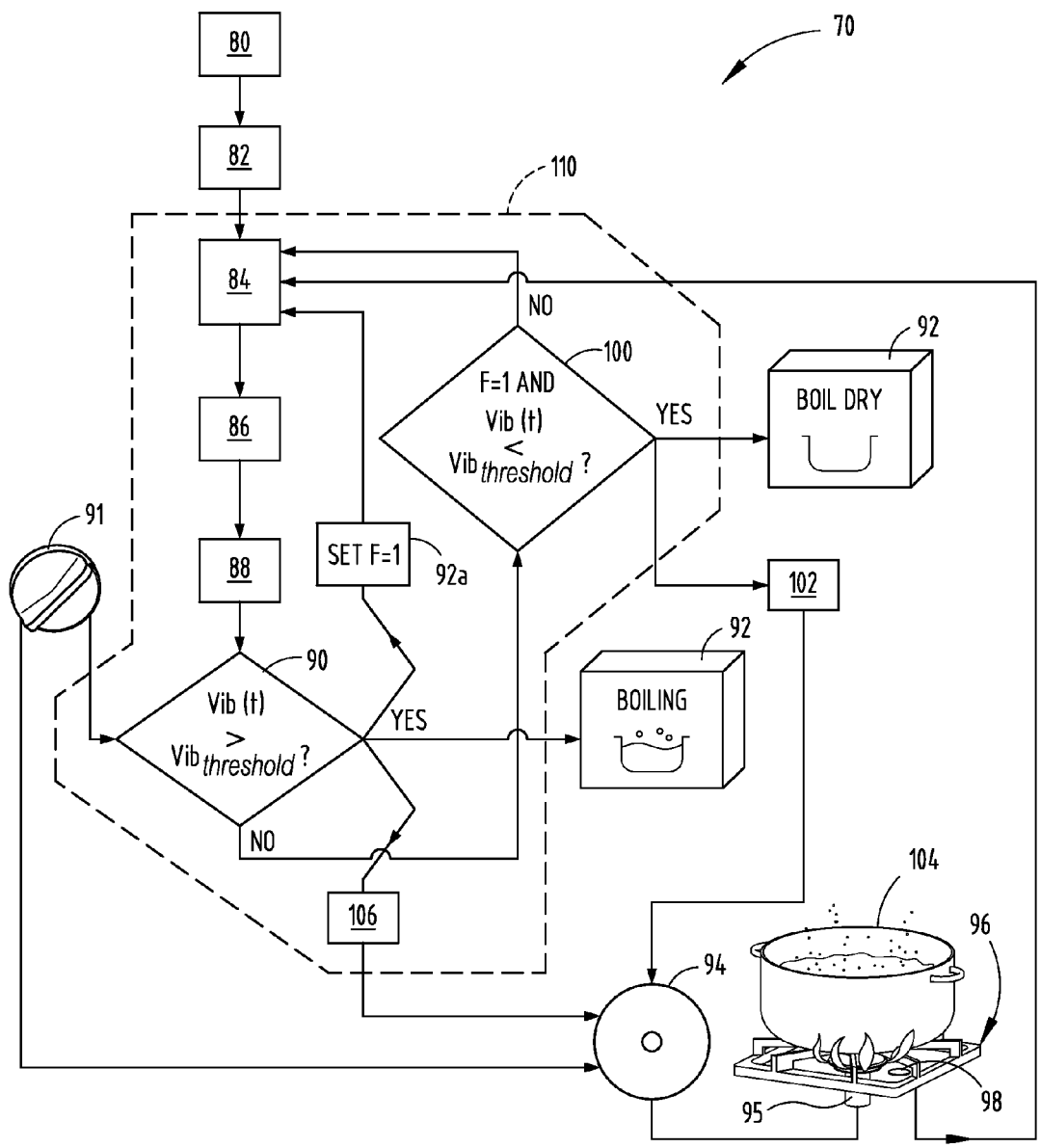
FIG. 3 is a flow chart schematic depicting a method of boil and boil-dry detection according to an additional embodiment.

The flow chart in FIG. 3 depicts a method 70 of boiling and boil-dry detection for cooking appliances. Step 80 is an initial step that relates to the placement of cookware (e.g., a pot 104) containing a food-related liquid on the cooking appliance. Step 82 is an initial step for operating a burner assembly 96 beneath the pot 104 to provide a heat input to the cookware. As shown in FIG. 3, an operator may rotate burner control knob 91 to supply a heat input to burner assembly control element 94. Burner control element 94 can then control the heat output from burner 95 used to heat cookware 104 containing a food-related liquid.

The method 70 for boiling and boil-dry detection may begin at Step 84, a step for detecting vibrations that correspond to the cookware (e.g., a pot 104) situated on the burner assembly 96 of the cooking appliance. Sensor assembly 98 (comparable to sensor assemblies 12 and 22 depicted in FIGS. 1, 1A), for example, can be used to generate vibration signals associated with such vibrations. As shown schematically in FIG. 3, a processor 110 (comparable to processors 30, 30a and 30b depicted in FIGS. 1-2B) can be employed to handle Step 84. The vibrations detected during Step 84 may originate from the physical placement of the cookware on the burner assembly during Step 80. They may also originate from the manual operation of the burner assembly on the cooking appliance itself in Step 82.

The next step in method 70, Step 86, relates to signal processing for the vibration data generated and detected during Step 84. Signal processing steps can be employed on this data by processor 110, for example, to filter noise and other artifacts out of the detected vibration data. Step 88 is for the collection and storage of vibration data related to the vibration signals generated and detected during Step 84. As shown schematically in FIG. 3, processor 110 can be employed to handle the signal processing and data collection Steps 86 and 88.

In Step 86, various signal processing approaches can be used to convert the vibration data detected in Step 84 into formats more useful for boiling and boil-dry determinations. For example, vibration data in the form of instantaneous vibration (including, but not limited to, acceleration) as a function of time can be directed through a low band pass filter. This filtering can help remove noise associated with those vibrations not associated with boiling and/or boil-dry conditions. For example, such noise can be generated by the rotation of knob 91 during Step 82. Such filtered data may also be subject to time-averaging to remove additional noise and perturbations. In one embodiment, the processed data can take the form of the absolute value of the raw vibration data minus the time-averaged filtered data set.

Another signal processing approach available in Step 86 is to apply Fast Fourier Transform (FFT) methodologies to the vibration data obtained in Step 84. Here, one goal may be the conversion of the vibration data (acceleration) vs. time into a data set that reflects vibration power vs. frequency. The objective of this signal processing approach is to take advantage of unique frequency distributions associated with different phenomena. For example, it is believed that the boiling condition is reflected in a higher, absolute range of frequencies than the frequency range associated with the placement of cookware 104 on burner assembly 96.

Steps 90 and 100 of method 70 can be sequenced for detecting boiling and boil-dry conditions for the food-related liquid contained in cookware 104. In particular, Steps 90 and 100 can make the boiling and boil-dry determinations based at least in part on the vibration data originating from Steps 84-88. As also depicted in FIG. 3, Steps 90 and 100 can be performed by processor 110.

In Step 90, the vibration data received, processed and collected in Steps 84-88 as a function of time, Vib(t), may be compared against a threshold value, $Vib_{threshold}$. The vibration data itself can be in the form of vibration including, but not limited to, acceleration data vs. time. The vibration data can also be subjected to signal processing steps (e.g., in Step 86) to convert the data to power vs. frequency. Either way, the vibration data can be compared against a predetermined threshold vibration level, absolute frequency range, resonant frequency range, harmonics and/or other prior-derived parameters in Step 90, to assess whether the level of the detected vibrations is indicative of a boiling condition. These thresholds, parameters and frequency ranges may correspond to prior-derived data associated with boiling of food-related liquids in cookware.

As such, Step 90 can be used to differentiate between vibration signals associated with the placement of cookware on the burner assembly (e.g., Step 80), physical operation of a heat input (e.g., Step 82), and boiling of the food-related liquid in cookware 104. If the vibration data, Vib(t), assessed in Step 90 exceeds the appropriate threshold, $Vib_{threshold}$, (or another prior-derived parameter), or falls within the prior-derived frequency range, a boiling condition can be judged to be present. As shown in FIG. 3, a "YES" results during Step 90 and a signal may be sent to an indicator element 92 to provide a visual and/or auditory indication of the boiling condition. In addition, method 70 proceeds to Step 92a, setting the flag parameter, F, equal to 1 (initially, F is set to a value of 0). Vibration data then continues to be collected as method 70 moves back to Step 84.

If the boiling criterion is not satisfied in Step 90, the detected vibration is not associated with a boiling condition. This situation corresponds to the "NO" result shown in FIG. 3. Since Step 90 has not been satisfied, method 70 now moves to Step 100. As shown in FIG. 3, Step 100 assesses whether or not a prior boiling condition has been determined in Step 90. In particular, Step 100 assesses whether the flag parameter, F, is set to a value equal to 1 from, for example, actions by Steps 90 and 92a. If no boiling has been previously observed in Step 90 (i.e., the flag parameter does not equal 1), Step 100 can produce a "NO" result. Accordingly, the vibration data continues to be collected in Step 84, and method 70 proceeds as shown in FIG. 3. This scenario, for example, can occur when the vibration data detected is associated with the physical placement of the cookware 104 on the cooking range or the operation of the burner control knob 91. Neither of these conditions corresponds to a boiling condition for the food-related liquid in cookware 104.

On the other hand, Step 100 may produce a "YES" result if a prior boiling condition had been observed in Step 90 (F is set to a value equal to 1), and the vibration data, Vib(t), falls below the threshold, $Vib_{threshold}$ (or falls outside of the prior-derived frequency range). A boil-dry condition may now be present (or the beginning of a boil-dry condition) and a signal may be sent to an indicator element 92 to provide a visual and/or auditory indication of the boil-dry condition. Under this scenario, Step 90 has detected that vibration levels have begun to subside below the prior-derived threshold level (or outside of the prior-derived frequency range and/or harmonics), and Step 100 confirms that a boiling condition had been previously observed. This is usually a sign that vaporization of food-related liquid in cookware 104 has occurred, which will usually lead to a boil-dry condition in a relatively short period of time.

FIG. 3 also depicts two optional Steps 102 and 106 of method 70 that can be instituted after the determination of boil-dry and boiling conditions, respectively. Upon the indication of a boil-dry condition in Step 100, method 70 may optionally proceed to Step 102, an override for the heat input to burner 95. In particular, Step 102 can be used to de-activate burner control element 94 to ensure that the cookware 104 is not damaged by the boil-dry condition. Similarly, upon the indication of a boiling condition in Step 90, method 70 may optionally proceed to Step 106. Step 106 allows for some additional control of burner control element 94 based on the observance of a boiling condition. For example, Step 106 may be used to reduce the energy input to burner 95 to conserve energy once a boiling condition has been detected.

Figure 4A:
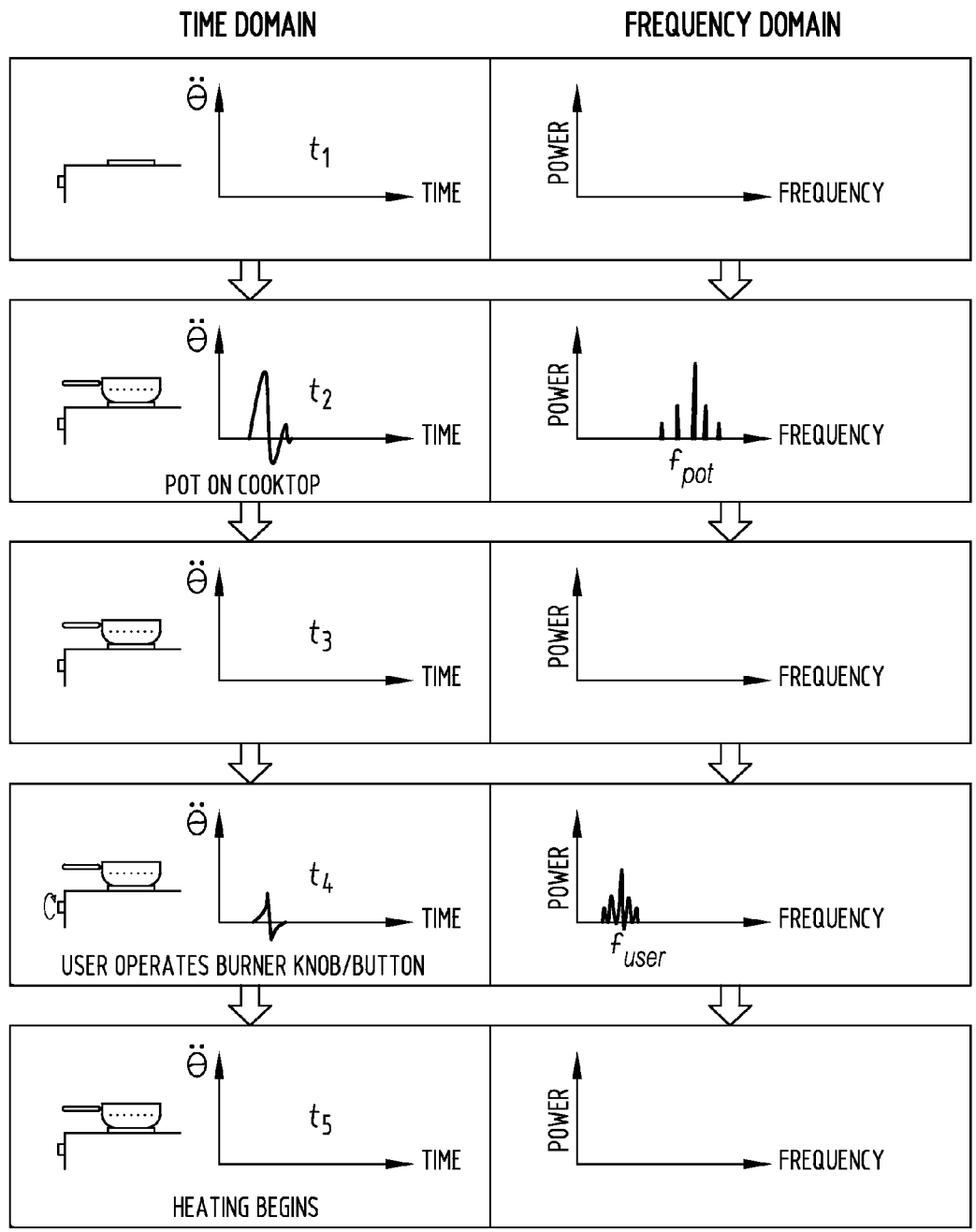
FIG. 4A is a schematic of the vibration and frequency signals obtained and processed by a cooking sensor system during the placement of a pot containing a food-related liquid onto a burner assembly according to an additional embodiment.
Figure 4B:
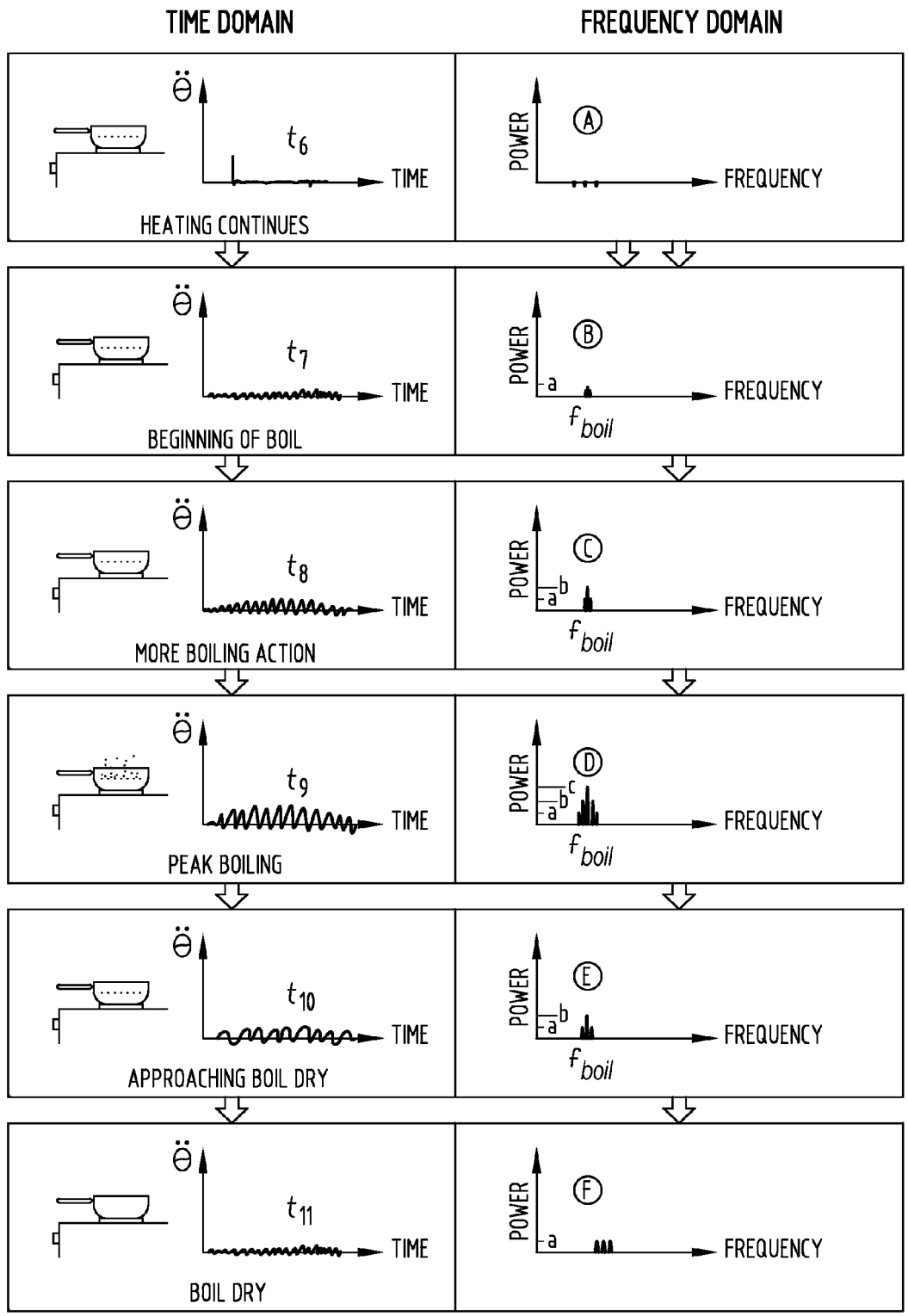
FIG. 4B is a schematic of the vibration and frequency signals obtained and processed by the cooking sensor system of FIG. 4A during the heating, boiling and boil-dry conditions of a food-related liquid in the pot.
Figure 4C:
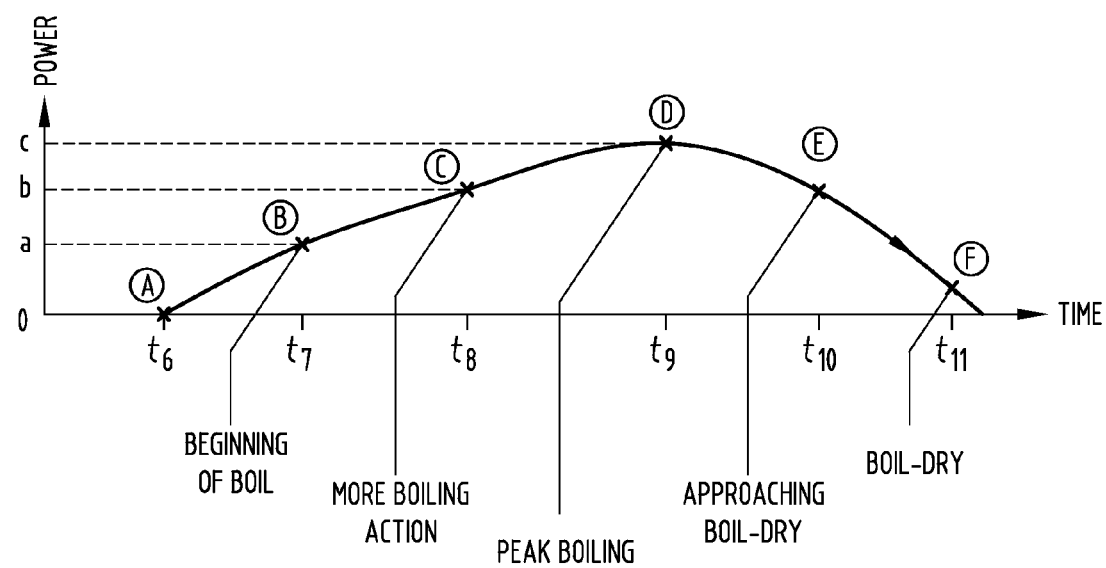
FIG. 4C is a schematic of the power (e.g., magnitude) of the obtained frequency signals as a function of time during the cooking operations depicted in FIGS. 4A and 4B.

FIGS. 4A-4C provide schematics of the vibration data obtained and processed by a cooking sensor system to determine boiling and boil-dry conditions according to another embodiment. In FIG. 4A, time domain and frequency domain vibration data are depicted as a function of time during the placement of a pot containing a food-related liquid onto a burner assembly. Moving from the top to the bottom of FIG. 4A (i.e., from time, t1, to time, t5), a pot is placed on the burner assembly of a cooktop; a user operates a heat input knob for the burner assembly; and then heating of the pot begins.

As shown in the time domain aspect of FIG. 4A, the placement of the pot on the cooktop, for example, at time, t2, can produce a relatively large vibration peak for a short duration. Further, the frequency domain for time, t2, shows that the introduction of the pot on the cooktop produces a relatively high frequency waveform. A processor, such as the processor 30 in FIGS. 1 and 1A, can assess such vibration data and determine that they do not correspond to boiling or boil-dry conditions associated with food-related liquid in the pot. Similarly, the movement or operation of a burner control knob, for example, at time, t4, can produce a relatively small vibration peak for a short duration in the time domain. The corresponding frequency domain data can be a relatively low frequency waveform. Again, a processor can assess such vibration data and determine that they relate to the physical aspect of adjusting the burner control knob, and not a boiling or boil-dry condition for the food-related liquid in the pot.

In FIG. 4B, time domain and frequency domain vibration data associated with the heating of a food-related liquid in the pot are depicted. The sequence of heating the pot filled with a food-related liquid occurs from time, t6, through time, t11. Boiling and boil-dry conditions are present at times, t7 and t11, respectively. As shown in FIG. 4B, the heating of the food-related liquid produces vibrations in the time domain with increasing magnitude. A processor can evaluate the vibration data over time. When the vibrations exceed a predetermined threshold for a specified duration at, for example, t7, the processor can determine that a boiling condition exists for the food-related liquid. In the frequency domain, the processor can evaluate the relative frequency of the vibration data to determine whether it corresponds to liquid boiling (rather than other vibration sources). Satisfying that test, the processor can next determine whether the magnitude of the frequency has reached a peak, e.g., at time, t9, that corresponds to a maximum or peak boiling condition. When the magnitude of the vibration data in the time domain (or the frequency peaks in the frequency domain) begins to subside below the threshold, e.g., at times, t10, and t11, the processor can evaluate this condition and determine that a boil-dry condition is now present.

Referring to FIG. 4C, the magnitude of the vibration data (i.e., power) produced during the cooking operations depicted in FIGS. 4A and 4B is plotted as a function of time. Point "B" of the curve (corresponding to time, t7) may reflect vibration data that has exceeded the threshold, indicative of the beginning of a boiling condition. Point "D" of the curve (corresponding to time, t9) may reflect the peak of the vibration data, corresponding to a peak boiling condition. Once the vibration data begins to exhibit a decrease in magnitude below the threshold, e.g., at point "E" (at time, t10), the boiling of the food-related liquid has begun to subside. This condition, as described earlier, can be indicative of the beginning of a boil-dry condition. At point "F," the magnitude of the vibration data has approached zero, thus corresponding to a boil-dry condition.

One advantage of the present cooking sensor system is that it offers better control of boiling operations to reduce spattering, over-cooking and other-related food waste. Another benefit provided by the sensor systems described herein is a reduced likelihood of cookware damage during the boiling operation. An additional benefit of these sensor systems is that an operator can more efficiently conduct boiling operations, using less energy than possible through conventional methods.

Other variations and modifications can be made to the aforementioned structures and methods without departing from the concepts of the present disclosure. These concepts, and those mentioned earlier, are intended to be covered by the following claims unless the claims by their language expressly state otherwise.

We claim:

1. A method of boil and boil-dry detection for cooking appliances, comprising the steps:
   detecting vibrations that correspond to cookware situated on a burner assembly;
   generating a vibration signal based on the vibrations;
   performing signal processing on the vibration signal;
   collecting vibration data related to the vibration signal; and
   detecting boiling and boil-dry conditions for a liquid contained within the cookware based at least in part on an evaluation of the vibration data,
   wherein the step of detecting boiling and boil-dry conditions for a liquid contained within the cookware is based at least in part on amplitude and time components of the vibration data, and
   further wherein the step of detecting each of the boiling and boil-dry conditions for a liquid contained within the cookware is based at least in part on a conversion of the vibration signal into a vibration data set comprising vibration power versus frequency by applying Fast Fourier Transform methodologies, and a comparison of the vibration data set to a predetermined threshold frequency, a predetermined boiling onset threshold vibration power, and a predetermined peak boiling threshold vibration power that correspond to prior-derived data associated with boiling and boil-dry conditions of the liquid in the cookware.

2. The method according to claim 1, wherein the step of detecting boiling and boil-dry conditions for a liquid contained within the cookware is also based in part on a detection of a heat input from the burner assembly.

3. A method of boil and boil-dry detection for cooking appliances, comprising the steps:
   detecting vibrations that correspond to cookware situated on a burner assembly;
   generating a vibration signal based on the vibrations;
   performing signal processing on the vibration signal;
   collecting vibration data related to the vibration signal;
   detecting boiling and boil-dry conditions for a liquid contained within the cookware based at least in part on an evaluation of the vibration data; and
   indicating the boiling and boil-dry conditions
   wherein the step of detecting boiling and boil-dry conditions for a liquid contained within the cookware is based at least in part on amplitude and time components of the vibration data, and
   further wherein the step of detecting each of the boiling and boil-dry conditions for a liquid contained within the cookware is based at least in part on a conversion of the vibration signal into a vibration data set comprising vibration power versus frequency by applying Fast Fourier Transform methodologies, and a comparison of the vibration data set to a predetermined threshold frequency, a predetermined boiling onset threshold vibration power, and a predetermined peak boiling threshold vibration power that correspond to prior-derived data associated with boiling and boil-dry conditions of the liquid in the cookware.

4. The method according to claim 3, wherein the step of detecting boiling and boil-dry conditions for a liquid contained within the cookware is also based in part on a detection of a heat input from the burner assembly.

5. A method of boil and boil-dry detection for cooking appliances, comprising the steps:
   detecting vibrations that correspond to cookware situated on a burner assembly;
   generating a vibration signal based on the vibrations;
   performing signal processing on the vibration signal;
   collecting vibration data related to the vibration signal;
   detecting boiling and boil-dry conditions for a liquid contained within the cookware based at least in part on an evaluation of the vibration data; and
   controlling the burner assembly based at least in part on the boiling and boil-dry conditions, wherein the step of detecting boiling and boil-dry conditions for a liquid contained within the cookware is based at least in part on amplitude and time components of the vibration data, and further wherein the step of detecting each of the boiling and boil-dry conditions for a liquid contained within the cookware is based at least in part on a conversion of the vibration signal into a vibration data set comprising vibration power versus frequency by applying Fast Fourier Transform methodologies, and a comparison of the vibration data set to a predetermined threshold frequency, a predetermined boiling onset threshold vibration power, and a predetermined peak boiling threshold vibration power that correspond to prior-derived data associated with boiling and boil-dry conditions of the liquid in the cookware.

6. The method according to claim 5, wherein the step of detecting boiling and boil-dry conditions for a liquid contained within the cookware is also based in part on a detection of a heat input from the burner assembly.

* * * * *